US006268535B1

United States Patent
Moussa et al.

(10) Patent No.: US 6,268,535 B1
(45) Date of Patent: Jul. 31, 2001

(54) SYNTHESIS OF 3-ARYL-1-INDANAMINES

(75) Inventors: Adel M. Moussa, Burlington; Reem Haider, Woburn; Heather Taft, Littleton; Jurjus Jurayj, Acton; Weiheng Wang, Bedford; HaeSuk Suh, Allston, all of MA (US)

(73) Assignee: Pharm-Eco Laboratories, Inc., Devens, MA (US)

( * ) Notice: Subject to any disclaimer, the term of this patent is extended or adjusted under 35 U.S.C. 154(b) by 0 days.

(21) Appl. No.: 09/226,469

(22) Filed: Jan. 7, 1999

Related U.S. Application Data

(60) Provisional application No. 60/070,934, filed on Jan. 9, 1998.

(51) Int. Cl.[7] .................................................. C07C 211/00
(52) U.S. Cl. ........................... 564/307; 564/402; 562/491; 568/327
(58) Field of Search ...................................... 564/307, 402; 562/491; 568/327

(56) References Cited

U.S. PATENT DOCUMENTS

| | | |
|---|---|---|
| 5,639,913 | 6/1997 | Lidor et al. . |
| 5,877,218 | 3/1999 | Herzig et al. . |
| 5,877,221 | 3/1999 | Cohen et al. . |
| 5,880,159 | 3/1999 | Herzig et al. . |
| 5,914,349 | 6/1999 | Cohen et al. . |

FOREIGN PATENT DOCUMENTS

| | | |
|---|---|---|
| 23 39 715 A1 | 2/1975 | (DE) . |
| 0 035 363 A1 | 9/1981 | (EP) . |
| 0 076 669 A1 | 4/1983 | (EP) . |

OTHER PUBLICATIONS

Quallich, G.J., et al., "Friedel–Crafts Synthesis of 4–(3, 4–Dichlorophenyl)–3,4–dihydro–1(2H)–naphthalenone, a Key Intermediate in the Preparation of the Antidepressant Sertraline,"*J. Org. Chem.* 55:4971–4973 (1990).
Bogeso, K.P., "Neuroleptic Activity and Dopamine–Uptake Inhibition in 1–Piperazino–3–phenylindans," *J. Med. Chem.* 26: 935–947 (1983).
Bogeso, K.P., et al., "3–Phenyl–1–indanamines. Potential Antidepressant Activity and Potent Inhibition of Dopamine, Norepinephrine, and Serotonin Uptake," *J. Med. Chem.* 28:1817–1828 (1985).
Ganellin, C.R., "Indane and Indene Derivatives of Biological Interest," *Adv. Drug Res.* 4:163–249 (1967).
Barltrop, J.A., et al., "Compounds of Potential Pharmacological Interest. Part IV . Aryl and Alkyl Derivatives of 1–Aminoindane," *J. Chem. Soc.* No. 570:2928–2940 (156).
Feeman, J.F. and Amstutz, E.D., "3–Phenylindones. I. The Synthesis of 6–Chloro–3–(p–chlorophenyl)–1–indenone and Some Related Compounds," *J. Am. Chem. Soc.* 72:1522–1526 (1950).
Hyttel, J. and Larsen, J.–J., "Neurochemical Profile of Lu 19–005, a Potent Inhibitor of Uptake of Dopamine, Noradrenaline, and Serotonin," *J. Neurochem.* 44:1615–1622 (1985).
Xavier, L.C., et al., "(S)–Tetrahydro–1–Methyl–3, 3–diphenyl–1H,3H–Pyrrolo–[1,2–c][1,3,2]oxazaborole–borane complex," *Organic Syntheses 74:* 50–55 (1996).
Kuck, D., et al., Synthesis of Tribenzotriquinacene by Stereocontrolled Cyclization of Phenyl–Substituted $C_s$–Diindans (4bα,9,9aα,10–Tetrahydroindeno[1,2–α]indenes), *Chemische Berichte.* 127 (1):151–165 (1994).
Simons, J.H. and Archer, S., "Hydrogen fluoride as a condensing agent. VI. The alkylation of benzene with compounds containing an allylic group," *Chemical Abstracts* 33(15), Aug. 10, 1939.

*Primary Examiner*—Paul J. Killos
(74) *Attorney, Agent, or Firm*—Hamilton, Brook, Smith & Reynolds, P.C.

(57) ABSTRACT

The present invention is a method of preparing a 3-aryl-1-indanamine represented by structural formula I:

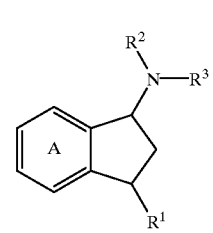

I.

and physiologically acceptable salts thereof.

In structure I, phenyl ring A can be unsubstituted or substituted with 1–4 substitutents.

$R^1$ is an aromatic group which can be substituted or unsubstituted.

$R^2$ and $R^3$ are each, independently, hydrogen, an aliphantic group, a substituted aliphatic group, an aromatic group, a substituted aromatic group, an aralkyl group, or a substituted aralkyl group. Alternatively, $R^2$ and $R^3$, taken together with the nitrogen substitutent on the indan ring, form a non-aromatic ring system having 1–2 heteroatoms.

32 Claims, No Drawings

SYNTHESIS OF 3-ARYL-1-INDANAMINES

RELATED APPLICATIONS

This application claims the benefit of U.S. Provisional Application No. 60/070,934, filed on Jan. 9, 1998, entitled "Synthesis of Trans-N,N-Dimethyl[3-(3',4'-Dichlorophenyl) Indan-1-yl] Ammonium Hydrogen Maleate," the entire teachings of which are incorporated herein by reference.

BACKGROUND OF THE INVENTION

Biogenic amines derived from the amino acid tyrosine (dopamine, norepinephrine, and epinephrine) and tryptophan (serotonin) are neurotransmitters that have been shown to be involved in disorders such as psychosis, depression, and Parkinson's disease. Chemicals that modulate the activity of one or more of these neurotransmitters can be used to treat the symptoms of these disorders. Trans-3-aryl-1-indanamines have been shown to be potent inhibitors of dopamine, norepinephrine and epinephrine uptake, while cis-3-aryl-1-indanamines have been shown to selectively inhibit the uptake of serotonin (Bogeso, et al, *J. Med. Chem.*, (1985), 28:1817).

Current synthetic routes to 3-aryl-1-indanamines produce a mixture of the regioisomers which must be separated. These methods typically are costly and time consuming.

SUMMARY OF THE INVENTION

The present invention is a method of preparing a 3-aryl-1-indanamine sented by structural formula I:

and physiologically acceptable salts thereof.

In structural formula I, phenyl ring A can be unsubstituted or substituted with 1-4 substitutents.

$R^1$ is an aromatic group which can be substituted or unsubstituted.

$R^2$ and $R^3$ are each, independently, hydrogen, an aliphantic group, a substituted aliphatic group, an aromatic group, a substituted aromatic group, an aralkyl group, or a substituted aralkyl group. Alternatively, $R^2$ and $R^3$, taken together with the nitrogen substitutent on the indan ring, form a non-aromatic ring system having 1-2 heteroatoms such as nitrogen, oxygen or sulfur.

The method of preparing a 3-aryl-1-indanamine represented by structural formula I comprises a first step of reacting, in the presence of a Friedel-Crafts catalyst and a proton source, a substituted or unsubstituted benzene, having at least two consecutive unsubstituted aromatic carbons, with a 3-aryl-1-prop-2-enoic acid to form a 3-aryl-3-phenyl-1-propanoic acid. 3-Aryl-1-prop-2-enoic acid and 3-aryl-3-phenyl-1-propanoic acid can be represented by structural formulas II and III, respectively:

The method further comprises a second step in which the 3-aryl-3-phenyl-1-propanoic acid (III) formed in step 1 is treated with a second Friedel-Crafts catalyst to form a 3-arylindan-1 -one represented by structural formula IV:

The method further comprises a third step in which the 3-arylindan-1-one (IV) formed in step 2 is reacted with a reducing agent to form a 3-arylindan-1-o1 represented by structural formula V:

The method further comprises a fourth step in which the 3-arylindan-1-o1(V) formed in step 3 is reacted with an activating agent in the presence of a base to form an activated 3-arylindan-1-o1.

The method further comprises a fifth step in which the activated 3-arylindan-1-o1 formed in step 4 is reacted with an amine compound represented by structural formula VI:

to form a 3-aryl-1-indanamine.

Another embodiment of the present invention is a method of forming a 3-phenyl-1-indanamine represented by structural formula VII:

VII.

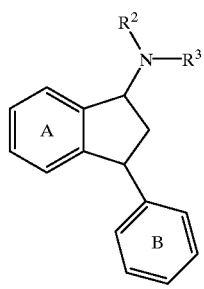

and physiologically acceptable salts thereof

Rings A and B are each, independently, substituted or unsubstituted. Ring A can be unsubstituted or can have 1–4 substitutents, and ring B can be unsubstituted or can have 1–5 substitutents.

$R^2$ and $R^3$ are defined as above.

The method of preparing a 3-phenyl-1-indanamine represented by structural formula VII comprises a first step of reacting, in the presence of sulfuric acid, a substituted or unsubstituted benzene, having at least two consecutive unsubstituted aromatic carbons, with a 3-phenyl-1-prop-2-enoic acid to form a 3,3-diphenyl-1-propanoic acid. 3-Phenyl-l-prop-2-enoic acid and 3,3-diphenyl-1-propanoic acid can be represented by structural formulas VIII and IX, respectively:

VIII.

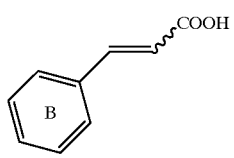

IX.

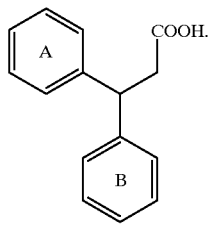

The method further comprises a second step of treating the 3,3-diphenyl-1-propanoic acid (IX) formed in step 1 with chlorosulfonic acid to form a 3-phenylindan-1-one represented by structural formula X:

X.

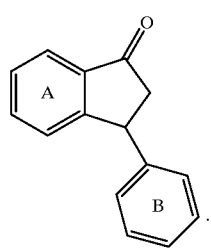

The method further comprises a third step of reacting the 3-phenylindan-1-one (X) formed in step 2 with sodium borohydride to form a 3-phenylindan-1-ol represented by structural formula XI:

XI.

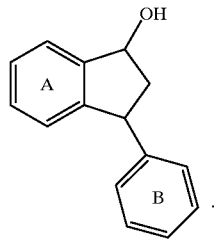

The method further comprises a fourth step in which the 3-phenylindan-1-ol (XI) formed in step 3 is reacted with an aliphatic or aromatic sulfonyl chloride in the presence of a base to form a 3-phenylindan-1-sulfonate ester represented by structural formula XII:

XII.

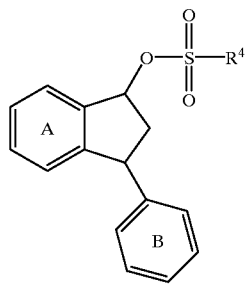

wherein $R^4$ is a substituted or unsubstituted aliphatic or aromatic group.

The method further comprises a fifth step in which the 3-phenylindan-1-sulfonate ester (XII) formed in step 4 is reacted with an amine compound represented by structural formula VI to form the 3-phenyl-1-indanamine (VII).

Another embodiment of the present invention is a method of preparing a 3-phenyl indan-1 -one represented by structural formula X. The method comprises a first step of reacting, in the presence of a first Friedel-Crafts catalyst and a proton source, a compound represented by structural formula VIII with a substituted or unsubstituted benzene having at least two consecutive unsubstituted aromatic carbons to form a 3,3-diphenyl-1-propanoic acid (IX), and a second step in which the 3,3-diphenyl-1-propanoic acid (IX) is converted to a 3-phenylindan-1-one (X) by treatment with a second Friedel-Crafts catalyst.

Another embodiment of the present invention is a method of preparing a 3-phenyl indan-1-ol represented by structural formula XI. The method comprises three reaction steps. In the first step, a compound represented by structural formula VIII is reacted, in the presence of a first Friedel-Crafts catalyst and a proton source, with a substituted or unsubstituted benzene having at least two consecutive unsubstituted aromatic carbons to form a 3,3-diphenyl-1-propanoic acid (IX). In the second step, the 3,3-diphenyl-1-propanoic acid (IX) is converted to a 3-phenylindan-1-one (X) by treatment with a second Friedel-Crafts catalyst. In the third step, the 3-phenyl indan-1-one (X) is reacted with a reducing agent to form a 3-phenylindan-1-ol (XI).

Another embodiment of the present invention is a method of preparing a 3-phenylindan-1-one represented by structural formula X. The method comprises the step of treating a 3,3-diphenyl-1-propanoic acid (IX) with a Friedel-Crafts catalyst.

Another embodiment of the present invention is a method of preparing a 3-phenyl-1-indanamine represented by structural formula VII. The method comprises a first step in which a 3-phenylindan-1-ol (XI) is reacted with an activating agent in the presence of a base to form an activated 3-phenyl-1-indanamine, and a second step in which the activated 3-phenyl-1-indanamine is reacted with an amine compound represented by structural formula VI to form the 3-phenyl 1-indanamine (VII).

3-Aryl-1-indanamines are potent inhibitors of dopamine, norepinephrine, epinephrine and serotonin uptake, and therefore, expected to be useful in treating disorders such as psychosis, depression and Parkinson'disease. The method described herein allows 3-aryl-1-indanamines to be synthesized in high yields with fewer reaction steps than previously described methods. In addition, trans-3-aryl-1-indanamines can be selectively prepared by the method of the invention.

DETAILED DESCRIPTION OF THE INVENTION

The features and other details of the method on the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

A schematic representation of the method of preparing a 3-aryl-1-indanamine can be seen in Scheme I. The first step is a Friedel-Crafts alkylation in which a benzene adds to a double bond. Dialkylation is minimized by using excess benzene. A proton source is necessary for the reaction, therefore protonic Friedel-Crafts catalysts are preferred. A proton source is a compound that has acidic protons, such as organic or inorganic acids.

The second step is a Friedel-Crafts acylation to close the five membered ring. This reaction can proceed by converting the carboxylic acid into an acid chloride followed by treatment with a Lewis acid, or the carboxylic acid can be added directly to ring A by treatment with a protonic Friedel-Crafts catalyst.

A Friedel-Crafts catalyst can be a Lewis acid (i.e., and electron acceptor) or a protonic acid (i.e., a proton donor). Protonic acids are preferred for the Friedel-Crafts alkylation of step 1. Examples of protonic acid catalysts include inorganic acids such as anhydrous sulfuric acid or hydrogen fluoride. Examples of Lewis acids that can catalyze Friedel-Crafts alkylations and acylations include $AlBr_3$, $AlCl_3$, $GaCl_3$, $FeCl_3$, $SbCl_5$, $ZrCl_4$, $SnCl_4$, $BCl_3$, $BF_3$, $SbCl_3$.

In the third reaction step, the ketone is reacted with a reducing agent to form an alcohol. A reducing agent, as used herein, is a chemical or combination of chemicals that will convert the ketone to an alcohol. Suitable reducing agents include sodium borohydride, lithium borohydride, borane, disiamylborane, 9-bora-bicyclo[3.3.1]nonane, lithium tri-tert-butoxyaluminohydride aluminum hydride, lithium triethylborohydride, and lithium tri(sec-butyl)borohydride. Preferred reducing agents selectively convert the 3-arylindan-1-one into a cis-3-arylindan-1-ol. Sodium borohydride is a preferred reducing agent.

Other reducing agents suitable for preferentially forming either cis or trans 3-arylindan-1-ol include combinations of a carbonyl reducing agent, such as lithium aluminum hydride, lithium borohydride or sodium borohydride, with an optically pure compound, such as an amino alcohol, sugar or hydroxyalkaloid. Typically, a chiral reducing agent is about 25% to about 75% (w/w) carbonyl reducing agent and about 25% to about 75% (w/w) optically active compound. Other suitable reducing agents suitable for preferentially forming either a cis or trans 3-arylindan-1-ol include 2,5-dimethylborolane, as described in Imai et al., *J. Am. Chem. Soc.*, 108:7402 (1986), K-glucoride, as described in Brown et al., *J. Org. Chem.*, 53:1231 (1988), NB-Enantride, as described in Midland et al., *J. Org. Chem.*, 56:1068 (1991), borane with a chiral oxazaborolidine catalyst, as described in Corey et al., *J. Am. Chem. Soc.*, 109:7925 (1987), and R-Alpine-Hydride and S-Alpine-Hydride, obtainable from Aldrich Chemical Co.

Alternatively, preferential formation of a cis or trans 3-arylindan-1-ol can occur through the use of a sterically large (or bulky) carbonyl agent.

In the fourth step, the 3-arylindan-1-ol is reacted with an activating agent. An activating agent, as used herein, is a compound that can react with an alcohol in the presence of a base to convert the alcohol into a good leaving group. Suitable activating agents include thionyl chloride or substituted or unsubstituted aliphatic or aromatic sulfonyl chlorides, for example, trifluoromethanesulfonyl chloride. Suitable bases include hindered organic bases such as trialkyl amines. Preferred activating groups can react with the 3-arylindan-1-ol such that it retains its chiral configuration at the C-1 position. A particularly preferred activating agent and base combination is a substituted or unsubstituted aliphatic or aromatic sulfonyl chloride and a trialkyl amine.

In the fifth step, an amine compound is reacted with the activated 3-arylindan-l-ol. An amine compound, as used herein, is ammonia or a compound that has a primary or secondary amine. The amine can be part of a ring system. For example, piperazine, pyrrolidine, piperidine, morpholine and piperidinopiperidine. Amine compounds that react with the activated 3-arylindan-1-ol and invert the chiral configuration at the C-1 position are preferred. For example, an amine compound that reacts with an activated cis-3-arylindan-1-ol to form a trans-3-aryl-1-indanamine is preferred. Piperazines are particularly preferred amine compounds.

The 3-aryl-1-indanamine is obtained as the free base which can be converted to a salt by recrystalization with an acid such as maleic acid. Physiologically acceptable salts are preferred. An enantiomerically pure chiral acid, such as L-(+) or D-(–) tartaric acid, can be used to resolve the (1S, 3R) and (1R, 3S) enantiomers of 3-aryl-1-indanamine by selective recrystalization of the salt. The salt can be converted back to the free base by treating with a basic solution, such as an aqueous sodium bicarbonate solution, followed by extraction of the enantiomerically pure 3-aryl-1-indanamine with an organic solvent.

Scheme I
Synthesis of 3-aryl-1-indanamine.

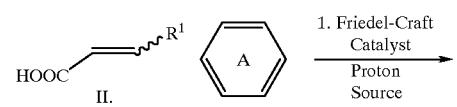

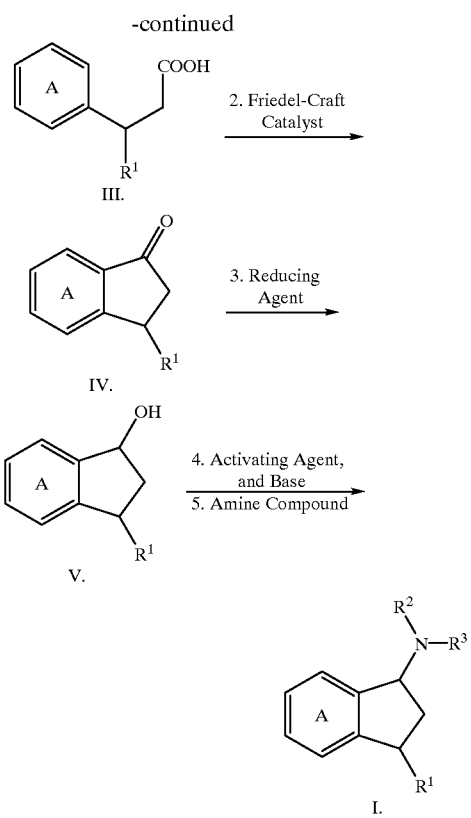

Aliphatic groups, as used herein, include straight chained or branched $C_1-C_{18}$ hydrocarbons which are completely saturated or which contain one or more units of unsaturation, or cyclic $C_3-C_{18}$ hydrocarbons which are completely saturated or which contain one or more unconjugated double bonds. Lower alkyl groups are straight chained or branched $C_1-C_6$ hydrocarbons or $C_3-C_6$ cyclic hydrocarbons which are completely saturated.

Aromatic groups include carbocyclic ring systems (e.g. benzyl) and fused polycyclic, carbocyclic ring systems (e.g. naphthyl, anthracenyl or 1,2,3,4-tetrahydronaphthyl). In addition, aromatic groups include heteroaryl ring systems (e.g., thiophene, furan, pyrroles, or pyrans) and heteroaryl ring systems in which a carbocyclic aromatic ring, a carbocyclic non-aromatic ring or heteroaryl ring is fused to one or more other heteroaryl rings. For example, benzimidazole, thianaphthene, benzofuran, or indole. An aryl group is a carbocyclic aromatic ring system or a polycyclic, carbocyclic aromatic ring system.

An aralkyl group is an aromatic substituent that is linked to a compound by an aliphatic group having from one to four carbon atoms.

Suitable substitutents include aliphatic groups, halogenated aliphatic groups, aromatic groups, aralkyl groups, halogens, trihalomethyl, cyano, and nitro. Other suitable substitutents include $R^6O-$, $R^6OC(O)-$, $R^6C(O)-$, $R^6C(O)O-$, $R^6S-$, $R^6S(O)-$, $R^6S(O)_2-$, $R^6S(O)_2O-$, $R6R^7N-$, $R^6R^7NC(O)-$, $R^6HNC(O)NH-$, or $R^6C(O)NH-$, wherein $R^6$ and $R^7$ are each, independently, hydrogen, a lower alkyl group, an aryl group and and aralkyl group.

In a preferred embodiment, ring A is substituted with one to four activating substitutents. An activating substituent is a substituent that is an electron donor, and therefore, increases the electron density of the aromatic ring. Examples of activating substitutents include aliphatic groups, aromatic groups, aralkyl groups, $R^6O-$, and $R^6S-$.

In another preferred embodiment, the aromatic group represented by $R^1$ is substituted with a deactivating substitutent. A deactivating substitutent is an electron withdrawing substituent. Electron withdrawing substitutents decrease the electron density of the aromatic ring. Examples of deactivating substitutents include halogens, trihalomethyl, cyano, nitro, $R^6OC(O)-$, $R^6C(O)-$, $R^6S(O)-$, $R^6S(O)_2-$ and $R^6R^7NC(O)-$.

In another preferred embodiment, ring B is substituted with a deactivating substitutent.

EXEMPLIFICATION

EXAMPLE 1

Synthesis of 3-(3',4'-Dichlorophenyl) 3-Phenylpropanoic Acid

A mixture of 3,4-dichlorocinnamic acid (50 g, 0.23 mole), benzene (150 mL) and concentrated sulfuric acid (100 mL) was stirred (using air driven overhead stirrer) in a 500 mL 3-neck round bottom flask while maintaining a reaction temperature of 85–95° C. The progress of the reaction was followed by HPLC. When the level of 3,4-dichlorocinnamic acid was <1% by HPLC (approximately 24 h), the reaction mixture was cooled to room temperature, then slowly poured into ice (300 g). The mixture was stirred for 30 min. then transferred into a 2 L separatory funnel. The organic layer was separated from the aqueous layer, and the aqueous layer was extracted with ethyl acetate (2×300 mL). The organic layers were combined, washed with water (5×500 mL) and brine (2×400 mL), then concentrated under reduced pressure. Ethyl acetate (500 mL) was added to the concentrate and the solution was evaporated to dryness. The product was dried under high vacuum at room temperature for 24 h. The desired carboxylic acid was obtained as a thick oil (65.8 g, 96% yield).

EXAMPLE 2

Synthesis of 3-(3',4'-Dichlorophenyl) Indan-1-one

Chlorosulfonic acid (66 mL, 0.99 mole) was added slowly to a stirring solution of 3-(3',4'-dichlorophenyl) 3-phenylpropanoic acid (65 g, 0.22 mole) in dichloromethane (330 mL) at room temperature. After 30 min., the reaction was monitored by TLC against authentic sample of 3-(3',4'-dichlorophenyl) 3-phenylpropanoic acid. If the reaction was not complete, an additional 10–20 mL of chlorosulfonic acid was added and the reaction was stirred for an additional 30 min. When the reaction was complete, the mixture was slowly poured into ice (400 g), stirred for 15 min., then transferred to a 1 L separatory funnel. The organic layer was drained and the aqueous layer was extracted with ethyl acetate (2×400 mL). The combined organic layers were washed with water (5×500 mL) and brine (2×400 mL), then concentrated under reduced pressure. A mixture of ethyl acetate:heptane (1:9) (100 mL) was added to the concentrate and the solution was stirred for one hour at room temperature. The temperature was lowered to 5°–10°C. and stirring was continued for 4 hours. The precipitate was recovered by filtration and washed with a cold solution (2×100 mL) of 1:9 ethyl acetate:heptane. The off-white solid was dried under high vacuum for 16 h to obtain 45.6 g (71%) of product. The 3-(3',4'-dichlorophenyl) indan-1-one was 97% pure by HPLC.

EXAMPLE 3

Synthesis of Cis-3-(3',4'-Dichlorophenyl)indan-1-ol

A solution of 3-(3',4'-dichlorophenyl)indan-1-one (25 g, 0.09 mole) in 250 mL of tetrahydrofuran (hereinafter "THF") was stirred at −5° C. In a separate flask, a solution of sodium borohydride (6.8 g, 0.18 mole) in water (28 mL) was cooled to 0°C., then added dropwise to the solution of 3-(3',4'-dichlorophenyl)indan-1-one, maintaining the temperature of the reaction mixture between −5–0° C. After addition of the sodium borohydride solution was complete, the cooing bath was removed and the reaction mixture was stirred for 2 h. The reaction was monitored by TLC against an authentic sample of cis-3-(3',4'-dichlorophenyl)indan-1-ol and an authentic sample of 3-(3',4'-dichlorophenyl)indan-1-one. When the starting material disappeared, 150 mL of ice-cold water was added to quench the reaction. After stirring for 1 h, THF was removed under reduced pressure, and the mixture was extracted with ethyl acetate (2×300 mL). The ethyl acetate layer was washed with water (2×250 mL) and brine (2×200 mL), then concentrated under reduced pressure to obtain an oily product. A solution (100 mL) of 1:9 ethyl acetate:heptane was added to the concentrate and stirred for 1 h at room temperature, then at 5°–10° C. for 4 h. The precipitated product was collected by filtration, then washed with an ice-cold solution (120 mL) of 1:9 ethyl acetate:heptane. After drying the solid under high vacuum for 12 h, 18.8 g (74%) of 98.5% pure alcohol was obtained. The product contained ≦1% of the undesired trans-alcohol.

EXAMPLE 4

Synthesis of Trans-1-(N,N-Dimethylamino) 3-(3',4'-Dichlorophenyl)indan

A solution of cis-3-(3',4'-dichlorophenyl)indan-1-ol(22.7 g, 0.081 mol) and triethylamine (45 mL, 0.325 mole) in THF (350 mL) was stirred (overhead stirring) under an inert atmosphere while maintaining a solution temperature of −15° C. In a separate flask under inert atmosphere, a solution of methanesulfonyl chloride (12.6 mL, 0.162 mol) in the THF (150 mL) was cooed to −60° C., then added slowly to the solution of cis-3-(3',4'-dichlorophenyl) indan-1-ol, maintaining the temperature of the reaction mixture below 0° C. After addition was complete, the reaction mixture was stirred for 10 min. at 0° C., then purged with dimethylamine gas (56 g, 1.21 mol). The reaction mixture was allowed to warm to room temperature and stirred for 5 h. The reaction was monitored by TLC against an authentic sample of cis-3-(3',4'-dichlorophenyl)indan-1-ol and against an authentic sample of trans-1-(N,N-dimethylamino) 3-(3',4'-dichlorophenyl)indan. When the reaction was complete, THF was removed under reduced pressure, and the mixture was extracted with ethyl acetate (250 mL). The ethyl acetate layer was removed, and the aqueous layer was extracted with ethyl acetate (2×100 mL). The combined ethyl acetate layers were washed with brine (2×100 mL) and dried over anhydrous sodium sulfate. The ethyl acetate solution was concentrated to give 26 g of 1-(N,N-dimethylamino)-3-(3',4'-dichlorophenyl)indan as a brown oil. The cis:trans isomeric ratio of the crude amine was 5:95 as determined by HPLC. The crude amine (26 g) was stirred with ethyl acetate (5 mL) for 10 min. After a solid started to form, heptane (45 mL) was added. The mixture was stirred for 1 hour at 15° C., then the precipitated product was collected by filtration, then washed with 40 mL of heptane. The product was dried under high vacuum to give 14 g of product (56%, first crop). The mother liquor was evaporated to an oil. A solution (15 mL) of 10% ethyl acetate in heptane was added to the oil and stirred for 1 hour at 15° C. The precipitated product was collected by filtration, then washed with 20 mL of heptane. The solid was dried under vacuum to give 5.2 g (21%, second crop). HPLC analysis indicated that the two crops contained the same ratio (0.6%) of the undesired cis isomer. The combined crops (19.2 g) were again stirred with a solution (40 mL) of 10% ethyl acetate in heptane for 1 hour at 15° C. The precipitated product was collected by filtration, then washed with 30 mL of heptane. The product was dried under high vacuum to give 15 g (60%) of 1-(N,N-dimethylamino) 3-(3',4'-dichlorophenyl) indan. Only 0.2% of the undesired cis isomer was detected by HPLC.

EXAMPLE 5

Synthesis of Trans-N,N-Dimethyl [3-(3',4'-Dichlorophenyl)indan-1-yl] Ammonium Hydrogen Maleate Trans-1-(N,N-dimethylamino)-3-(3',4'-dichlorophenyl) indan (13 g, 0.042 mole) was dissolved in ethanol (60 mL) at 50° C. In a separate flask, maleic acid (4.95 g, 0.042 mol) was dissolved in 20 mL of ethanol at 50° C., then added to the solution of trans-1-(N,N-dimethylamino)-3-(3',4'-dichlorophenyl)indan. The mixture was stirred at 50° C. for 1 h, then at 10° C. for 2 h. The precipitated product was collected by filtration, then washed with cold ethyl acetate (40 mL). The solid was dried under high vacuum to give 13.8 g (77%) of N,N-dimethyl [3-(3',4'-dichlorophenyl)indan-1-γ1] ammonium hydrogen maleate. The ratio of the undesired cis isomer was 0.3% as detected by HPLC.

The N,N-dimethyl [3-(3',4'-dichlorophenyl) indan-1-yl] ammonium hydrogen maleate salt was converted back to the free base by stirring it in an aqueous NaHCO$_3$ solution, then extracting 1-(N,N-dimethylamino)-3-(3',4'-dichlorophenyl) indan with ethyl acetate.

What is claimed is:

1. A method of preparing a 3-aryl-1-indanamine represented by the following structural formula:

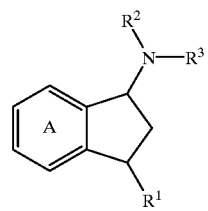

and physiologically acceptable salts thereof, wherein:

ring A is substituted or unsubstituted;

R$^1$ is a substituted or unsubstituted aromatic group;

R$^2$ and R$^3$ are each, independently, hydrogen, an aliphatic group, a substituted aliphatic group, an aromatic group, a substituted aromatic group, an aralkyl group, a substituted aralkyl group, or R$^2$ and R$^3$, taken together with nitrogen, form a non-aromatic ring system having 1–2 heteroatoms, said method comprising the steps of:

a) reacting, in the presence of a first Friedel-Crafts catalyst and a proton source, a substituted or unsubstituted benzene having at least two consecutive unsubstituted aromatic carbons, and a starting material represented by the following structural formula:

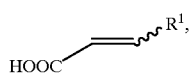

thereby forming a 3-aryl-3-phenyl-1-propanoic acid represented by the following structural formula:

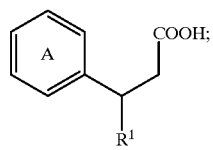

b) contacting said 3-aryl-3-phenyl-1-propanoic acid with a second Friedel-Crafts catalyst, thereby forming a 3-arylindan-1-one represented by the following structural formula:

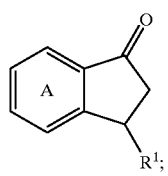

c) reacting said 3-arylindan-1-one with a reducing agent, thereby forming a 3-arylindan-1-ol represented by the following structural formula:

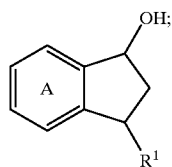

d) reacting said 3-arylindan-1-ol with an activating agent in the presence of a base, thereby forming an activated 3-arylindan-1-ol; and e) reacting said activated 3-arylindan-1-ol with an amine compound represented by the following structural formula:

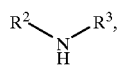

thereby forming said 3-aryl-1-indanamine.

2. The method of claim 1, wherein said 3-aryl-1-indanamine has a trans configuration.

3. The method of claim 2, wherein $R^1$ is a substituted or unsubstituted phenyl.

4. The method of claim 3, wherein said phenyl is substituted with 1 to 5 deactivating substituents.

5. The method of claim 4, wherein the deactivating substitutents are 3'-chloro and 4'-chloro groups.

6. The method of claim 1, wherein ring A is substituted with 1 to 4 activating substitutents.

7. The method of claim 1, wherein the first Friedel-Crafts catalyst is also the proton source.

8. The method of claim 7, wherein said first Friedel-Crafts catalyst is an inorganic acid.

9. The method of claim 8, wherein:
a) the inorganic acid is sulfuric acid;
b) the second Friedel-Crafts catalyst is chlorosulfonic acid;
c) the reducing agent is sodium borohydride;
d) the activating agent is a substituted or unsubstituted aliphatic or aromatic sulfonyl chloride; and
e) the amine compound is dimethyl amine.

10. A method of preparing a 3-phenyl-1-indanamine represented by the following structural formula:

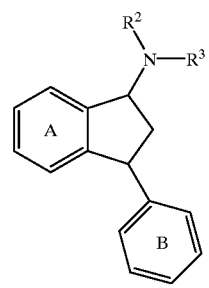

and physiologically acceptable salts thereof, wherein:
rings A and B are substituted or unsubstituted; and
$R^2$ and $R^3$ are each, independently, hydrogen, an aliphatic group, a substituted aliphatic group, an aromatic group, a substituted aromatic group, an aralkyl group, a substituted aralkyl group, or
$R^2$ and $R^3$, taken together with nitrogen, form a non-aromatic ring system having 1–2 heteroatoms, said method comprising the steps of:
a) reacting, in the presence of sulfuric acid, a substituted or unsubstituted benzene having at least two consecutive unsubstituted aromatic carbons, and a starting material represented by the following structural formula:

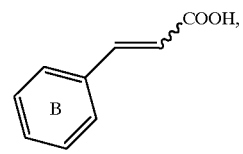

thereby forming a 3,3-diphenyl-1-propanoic acid represented by the following structural formula:

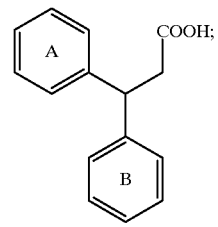

b) contacting said 3,3-diphenyl-1-propanoic acid with chlorosulfonic acid, thereby forming a 3-phenylindan-1-one represented by the following structural formula:

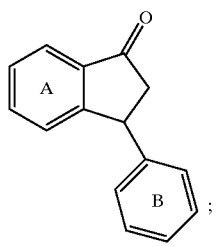

c) reacting said 3-phenylindan-1-one with sodium borohydride, thereby forming a 3-phenylindan-1-ol represented by the following structural formula:

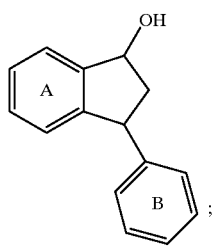

d) reacting said 3-phenylindan-1-ol with substituted or unsubstituted aliphatic or aromatic sulfonyl chloride in the presence of a base, thereby forming a 3-phenylindan-1-sulfonate ester represented by the following structural formula:

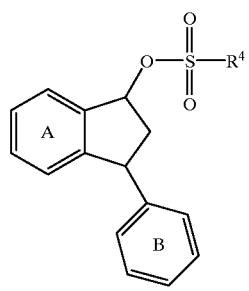

wherein $R^4$ is a substituted or unsubstituted aliphatic or aromatic group; and e) reacting said 3-phenylindan-1-sulfonyl ester with an amine compound represented by the following structural formula:

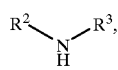

thereby forming said 3-phenyl-1-indanamine.

11. The method of claim 10, wherein said 3-phenyl-1-indanamine has a trans configuration.

12. The method of claim 11, wherein ring B is substituted with 1 to 5 deactivating substituents.

13. The method of claim 12, wherein the deactivating substitutents are 3'-chloro and 4'-chloro groups.

14. The method of claim 11, wherein ring A is substituted with 1 to 4 activating substitutents.

15. The method of claim 11 further comprising the step of:
f) contacting said trans-3-phenyl-1-indanamine with an acid, thereby forming a trans-3-phenyl-1-indanamine salt.

16. A method of preparing a 3-arylindan-1-one represented by the following structural formula:

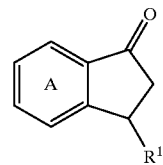

wherein:

$R^1$ is a substituted or unsubstituted aromatic group; and ring A is substituted or unsubstituted, said method comprising the steps of:

a) reacting, in the presence of a first Friedel-Crafts catalyst and a proton source, a substituted or unsubstituted benzene having at least two consecutive unsubstituted aromatic carbons, and a starting material represented by the following structural formula:

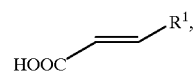

thereby forming a 3-aryl-3-phenyl-1-propanoic acid represented by the following structural formula:

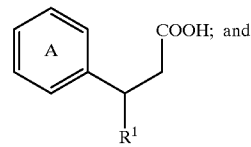

b) contacting said 3-aryl-3-phenyl-1-propanoic acid with a second Friedel-Crafts catalyst thereby forming said 3-arylindan-1-one.

17. The method of claim 16, wherein $R^1$ is a substituted or unsubstituted phenyl ring which is designated ring B, and the 3-arylindan-1-one formed is a 3-phenylindan-1-one.

18. The method of claim 17, wherein ring B is substituted with 1 to 5 deactivating substitutents.

19. The method of claim 18, wherein the deactivating substitutents are 3'-chloro and 4'-chloro groups.

20. The method of claim 17, wherein ring A is substituted with 1 to 4 activating substitutents.

21. The method of claim 17, wherein the first Friedel-Crafts catalyst is also the proton source.

22. The method of claim 21, wherein said first Friedel-Crafts catalyst is an inorganic acid.

23. The method of claim 22, wherein:

a) the inorganic acid is sulfuric acid; and b) the second Friedel-Crafts catalyst is chlorosulfonic acid.

24. A method of preparing a 3-arylindan-1-ol represented by the following structural formula:

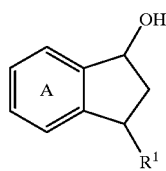

wherein:

R¹ is a substituted or unsubstituted aromatic group; and ring A is substituted or unsubstituted, said method comprising the steps of:

a) reacting, in the presence of a first Friedel-Crafts catalyst and a proton source, a substituted or unsubstituted benzene having at least two consecutive unsubstituted aromatic carbons, and a starting material represented by the following structural formula:

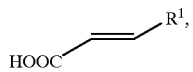

thereby forming a 3-aryl-3-phenyl-1-propanoic acid represented by the following structural formula:

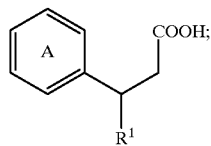

b) contacting said 3-aryl-3-phenyl-1-propanoic acid with a second Friedel-Crafts catalyst, thereby forming a 3-arylindan-1-one represented by the following structural formula:

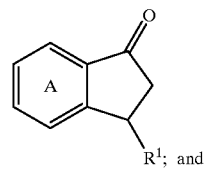

c) reacting said 3-arylindan-1-one with a reducing agent, thereby forming said 3-arylindan-1-ol.

25. The method of claim 24, wherein R¹ is a substituted or unsubstituted phenyl ring which is designated ring B, and the 3-arylindan-1-ol formed is a 3-phenylindan-1-ol.

26. The method of claim 25, wherein said 3-phenylindan-1-ol has a cis configuration.

27. The method of claim 26, wherein ring B is substituted with 1 to 5 deactivating substituents.

28. The method of claim 27, wherein the deactivating substitutents are 3'-chloro and 4'-chloro groups.

29. The method of claim 26, wherein ring A is substituted with 1 to 4 activating substitutents.

30. The method of claim 25, wherein the first Friedel-Crafts catalyst is also the proton source.

31. The method of claim 30, wherein said first Friedel-Crafts catalyst is an inorganic acid.

32. The method of claim 31, wherein:

a) the inorganic acid is sulfuric acid;

b) the second Friedel-Crafts catalyst is chlorosulfonic acid; and c) the reducing agent is sodium borohydride.

* * * * *